United States Patent [19]

Kappas et al.

[11] Patent Number: 5,010,073

[45] Date of Patent: * Apr. 23, 1991

[54] USE OF LIPOSOMES AS CARRIERS FOR METALLOPORPHYRINS

[75] Inventors: Attallah Kappas; George S. Drummond, both of New York, N.Y.

[73] Assignee: The Rockefeller University, New York, N.Y.

[*] Notice: The portion of the term of this patent subsequent to Apr. 14, 2004 has been disclaimed.

[21] Appl. No.: 485,174

[22] Filed: Feb. 26, 1990

Related U.S. Application Data

[63] Continuation-in-part of Ser. No. 417,298, Oct. 5, 1989, abandoned.

[51] Int. Cl.$^5$ .................. A61K 31/40; A61K 31/555; A61K 9/127; C07D 209/94
[52] U.S. Cl. .................................... 514/185; 514/410; 514/493; 514/505; 424/450
[58] Field of Search ............... 514/185, 410, 493, 505; 424/450

[56] References Cited

U.S. PATENT DOCUMENTS

| | | | |
|---|---|---|---|
| 4,649,151 | 3/1987 | Dougherty et al. | 514/410 |
| 4,657,902 | 4/1987 | Kappas et al. | 514/185 |
| 4,668,670 | 5/1987 | Rideout et al. | 514/185 |
| 4,684,637 | 8/1987 | Kappas et al. | 514/185 |
| 4,692,439 | 9/1987 | Rideout et al. | 514/185 |
| 4,692,440 | 9/1987 | Kappas et al. | 514/185 |
| 4,699,903 | 10/1987 | Rideout et al. | 514/185 |

Primary Examiner—Thurman K. Page
Assistant Examiner—C. Azpuru
Attorney, Agent, or Firm—Wyatt, Gerber, Burke & Badie

[57] ABSTRACT

Pharmaceutical copositions comprising liposomal metalloporphyrins are provided for parenteral administration to mammals, including humans. These liposomal metalloporphyrins selectively target the spleen and markedly inhibit the heme oxygenase activity therein. A method is also provided for intravenous administration of these compositions to mammals to selectively target the spleen.

20 Claims, 2 Drawing Sheets

USE OF LIPOSOMES AS CARRIERS FOR METALLOPORPHYRINS

RELATED APPLICATIONS

This application is a continuation-in-part of application Ser. No. 417,298 filed Oct. 5, 1989 now abandoned.

FIELD OF THE INVENTION

This invention relates generally to metalloporphyrins which are inhibitors of heme oxygenase in mammals and particularly to targeting of such inhibitors to selected body organs. More particularly, this invention relates to the parenteral administration of metalloporphyrins which are incorporated into liposomes in order to target the metalloporphyrin to selected body organs, principally the spleen.

The present invention is also directed to liposomal metalloporphyrin preparations (phospholipid vesicles), to therapeutically useful compositions containing such products, and to their use for treating various metabolic afflictions of mammals, particularly humans.

BACKGROUND OF THE INVENTION

Heme is a red pigment comprised of four sub-units called pyrroles which are chemically united to form a single large tetrapyrrole (porphyrin) ring structure. A metal ion is chelated at the center of this porphyrin. In higher organisms this metal is iron and the resulting structure is called iron protoporphyrin.

In physiological systems, heme is bound to certain proteins and these heme proteins bind oxygen at the site of the iron atom or they function as components of membrane bound electron transport systems. Cellular respiration, energy generation and chemical oxidation are dependent on these heme proteins.

In mammals and other vertebrates, heme is catabolized by the enzyme heme oxygenase to produce the bile pigment, bilirubin. Biliverdin is reduced to bilirubin by the action of the enzyme biliverdin reductase. In liver, bilirubin is converted to mono- and di-glucoronide conjugates which are excreted to the bile. The spleen is responsible for about 75 percent of bilirubin production, the remainder being produced in other body organs such as the liver and the kidneys, with the liver being responsible for 15-25 percent production of the total bilirubin. Bilirubin is a neurotoxic compound, but this toxicity does not normally present a serious problem in adults since, as was previously stated, bilirubin is converted to the corresponding di-glucoronide. The di-glucoronide is water soluble and is excreted. One of the more difficult aspects of the toxicity of bilirubin is the so-called jaundice of the newborn resulting from high concentrations of bilirubin in the blood serum of newborn mammals. Free bilirubin is fat soluble and readily crosses the blood-brain barrier causing extensive and serious brain damage. One manifestation of such toxicity in the brain is kernicterus or bilirubin encepthalopathy.

Elevated levels of bilirubin often appear in the serum of individuals with diseases such as congenital anemia, thalassemia and sickle cell anemia as well as various forms of liver disease. The concentration of bilirubin in the serum of such individuals, however, rarely reaches the high level found in neonates, although it can attain toxic levels which should be controlled.

The problem of bilirubin toxicity in mammals has received the attention of numerous investigators. Several recent patents, for example, have addressed this problem and disclosed therapeutic compositions which are used to decrease the rate at which heme is metabolized in mammals. A few of these patents, which are assigned to the assignee of the invention described herein, are discussed below.

U.S. Pat. No. 4,657,902 relates to the compound tin mesoporphyrin (SnMP) and therapeutic compositions containing the same used to inhibit heme metabolism in mammals, control the rate of tryptophan metabolism and increase the rate at which heme is excreted.

U.S. Pat. Nos. 4,668,670 and 4,692,439 are both directed to tin diiododeuteroporphyrin (SnDDP) for similar purposes.

U.S. Pat. No. 4,684,637 discloses the use of tin protoporphyrin (SnPP) for decreasing the rate of heme metabolism in mammals.

While the compounds disclosed in the foregoing patents cause a reduction in the catabolic activity of heme oxygenase, resulting in decreased bilirubin production, they would do so more efficiently if their concentration in the spleen could be increased. The spleen is the major producer of bilirubin. It is desirable, therefore, to increase the amount of active metalloporphyrin which reaches the spleen.

Attempts have been made to target the porphyrin compounds to different sites or organs in mammals. For example, G. Jori et al in their article on "Controlled Targeting of Different Subcellar Sites by Porphyrins in Tumor-bearing Mice," Brit. J. Cancer, Vol. 53, pp. 615-621 (1986), disclose that intraperitoneal injection of liposome-bound porphyrins to mice results in more efficient tumor targeting than that obtained by administration of the same porphyrins dissolved in homogeneous aqueous solutions. These investigators were not concerned with selective targeting of normal body organs of tissue enzymes. Indeed, in a later article on "Utilization of Liposomes and Low Density Lipoproteins and Porphyrin Carriers in Experimental Photodynamic Therapy," First International Conference on the Clinical Applications of Photosensitization for Diagnosis and Treatment, Tokyo, Japan (1986), Jori discloses that the administration of liposome-vehiculated hematoporphyrin (Hp) to the tumor tissue and to the organs of the reticuloendothelial system of mice did not result in any specificity of Hp localization although it did result in larger accumulation of Hp in the tumor.

While others have studied and reported on the use of liposomes as carriers for various drugs, so far as it is known none of these investigations have succeeded in selectively targeting a specific body organ or enzyme contained therein, to increase the concentration at the site of action of the porphyrin compound after it is administered to mammals.

It has also been demonstrated that certain metalloporphyrins are effective in decreasing bilirubin levels in various mammals, including rats, monkeys and humans. Table I below shows the effect of SnPP, and where indicated, CrPP and ZnPP on reduction of bilirubin levels in various mammals.

TABLE I

| ANIMAL MODEL & SPECIES | SnPP DOSE (umoles/kg) | BILIRUBIN/ CO REDUCTION (percent) |
|---|---|---|
| BILIARY CIRRHOSIS-MAN | 0.25-2.0 | 7-23 |
| GILBERT'S DISEASE-MAN | 0.5-1.8 | 29-43 |
| NORMAL ADULT-MAN | 1-2 | 38-47 |

TABLE I-continued

| ANIMAL MODEL & SPECIES | SnPP DOSE (umoles/kg) | BILIRUBIN/ CO REDUCTION (percent) |
|---|---|---|
| ABO INCOMPATIBILITY-MAN | 0.5 | 21–32 |
| NEONATAL MONKEY | 24–185 | 91 |
| NORMAL ADULT RAT | 10–50 | 24–30 |
| BILE DUCT LIGATED RAT | 100 | 62–70 |
| NEONATAL RAT | 10(CrPP) | 32 |
| NEONATAL RAT/ HEMATOMA | 65 | 25 |
| NEONATAL GUNN RAT | 50 | 19 |
| NORMAL ADULT RAT | 4–40(ZnPP) | 20–30 |

The data in Table I indicate that these metalloporphyrins inhibit heme oxygenase in humans, rats and monkeys, and thus appreciably reduce the bilirubin and/or bilirubin and carbon monoxide production rates. Where dosage ranges and bilirubin reduction ranges are given in the table, they represent the ranges for several mammals studied.

It has also been observed that following intravenous administration of SnPP into rats, the highest concentrations of SnPP were found in the liver and kidneys while the concentration of SnPP in the spleen was one-fourth of SnPP concentration in the liver. In addition, although splenic heme oxygenase was inhibited by 50–75%, the heme oxygenase activity was still high. It was, in fact, about the same as the heme oxygenase activity found in the livers of the control animals. The results of these studies are shown in Table II.

TABLE II

| ITEM | KIDNEY | LIVER | SPLEEN |
|---|---|---|---|
| CONCENTRATION OF SnPP IN ORGAN @ 24 HOURS | | | |
| (A) HOMOGENATE ($\mu$M) | 99.3 ± 1/5* | 27/0 ± 1.8 | 6.5 ± 0.6 |
| (B) MICROSOMES (pm/mg. protein) | — | 146–284 | 60 –90 |
| HEME OXYGENASE ACTIVITY (nm bilirubin/hr/mg. protein) | | | |
| (A) PRIOR TO TREATMENT | 1.8 ± 0.2 | 2.7 ± 0,3 | 12.4 ± 0.4 |
| (B) 24 HOURS AFTER TREATMENT WITH AQUEOUS SnPP | 0.6 ± 0.1 | 0.3 ± 0.04 | 2.3 ± 0.3 |

*Mean ± SE for 3–4 rats

Despite all of the studies and efforts described above, the problem of targeting active porphyrins to the spleen where they would be most effective in binding and inhibiting the enzyme, heme oxygenase, remains unsolved.

Accordingly, it is an object of this invention to inhibit or substantially reduce the catabolic action of heme oxygenase in mammals.

It is another object of this invention to inhibit or substantially reduce the catabolic action of heme oxygenase in a selected body organ of mammals, notably humans.

It is a further object of this invention to inhibit or substantially reduce the catabolic action of heme oxygenase in a selected body organ by the administration of a porphyrin compound bound to liposome.

It is still another object of this invention to inhibit or substantially reduce the catabolic action of heme oxygenase in the spleen of mammals by selectively targeting the spleen with a liposome-porphyrin product administered to the mammals.

It is also an object of this invention to increase the concentration of heme oxygenase activity inhibiting porphyrins in the spleen of mammals by administering a liposome porphyrin product to the mammal and selectively targeting the heme oxygenase in the spleen.

The foregoing and other objects and features of the present invention will be more clearly comprehended from the following detailed description of the invention taken together with the accompanying drawings.

SUMMARY OF THE INVENTION

Figure 1:
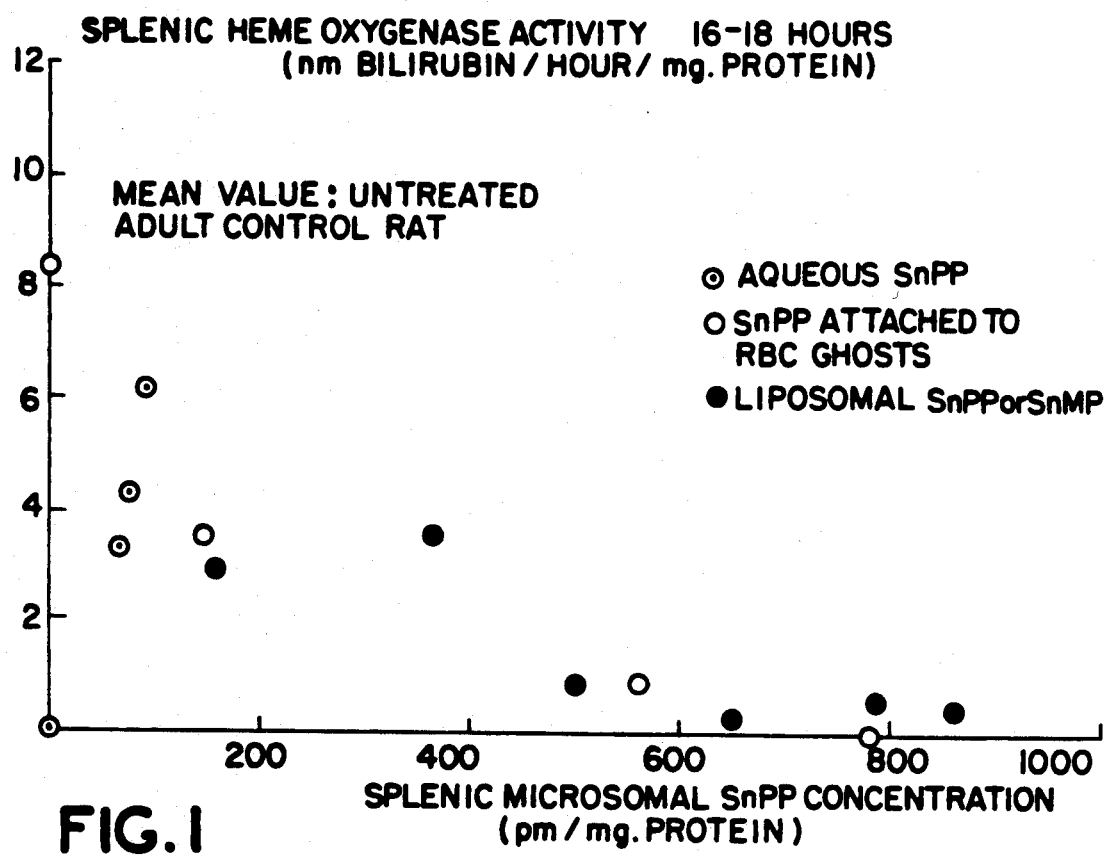
FIG. 1 is a graph illustrating the effect of SnPP and, for the sake of comparison, incorporated within liposomal red blood cell ghosts, on the inhibition of splenic heme oxygenase after 16–18 hours in adult rats.

In accordance with this invention, SnPP, SnMP SnDDP as well as the corresponding zinc (Zn), chromium (Cr) and manganese (Mn) inhibitors of heme oxygenase, or mixtures thereof, may be bound to or incorporated in liposomes to produce products which upon parenteral administration to mammals, including humans, will preferentially target the spleen thereby improving the efficiency with which the metalloporphyrins inhibit the activity of heme oxygenase, decreasing the rate of metabolism of heme, and the systemic accumulation of bilirubin. Although the active compound selectively targets the spleen, some of it is distributed throughout the body especially to the liver and femoral marrow. The overall result is a more rapid onset and marked improvement in heme oxygenase inhibition compared to the metalloporphyrins administered in aqueous solutions.

The liposomal metalloporphyrins may be administered alone or with any of a wide variety of pharmaceutical excipients, the selection of which is well within the skill of the art.

DETAILED DESCRIPTION OF THE INVENTION

It has now been surprisingly discovered that when certain metalloporphyrins are bound to or incorporated in liposomes and the resulting liposomal metalloporphyrin is administered to mammals, splenic heme oxygenase will be much more inhibited than if the metalloporphyrin is administered in aqueous solution. It has also been surprisingly discovered that when liposomal metalloporphyrin is administered to mammals in accordance with this invention, the majority of the metalloporphyrin is taken up by the spleen, rather than by the liver or the kidneys as is the case when the metalloporphyrin is administered alone. The ability of the compounds of the present invention to target the spleen constitutes an advance over the art and offers a unique method of improving the inhibition and reduction of splenic heme oxygenase activity, thereby improving the reduction of the undesired bilirubin level in the mammalian system. The improvement in reduction of bilirubin levels in jaundiced newborns constitutes a major clinical advance in the treatment of this disease.

SnPP, SnMP and SnDDP constitute the metalloporphyrins of choice in the practice of this invention. However, other metalloporphyrins which inhibit heme oxygenase activity with a resultant decrease in bilirubin production can also be employed in the practice of this invention. These include zinc protoporphyrin (ZnPP), chromium protoporphyrin (CrPP) and manganese protoporphyrin (MnPP) as well as the corresponding mesoporphyrins and diiododeuteroporphyrins. Another heme oxygenase inhibitor which may be used in the practice of this invention is zinc deuteroporphyrin 2,4-bis glycol.

In accordance with the present invention, the metalloporphyrin compound is bound to or incorporated in the liposomes which serve as vehicles for targeting these compounds to the spleen. The resulting liposome-bound metalloporphyrin is then administered intravenously (IV) into the mammal in effective dosage. The methods of incorporating the metalloporphyrin compound into liposome are described below.

MATERIALS AND METHODS

Animals

Adult male Sprague-Dawley rats were obtained from Taconic Farms, Germantown, N.Y. The rats were housed in The Rockefeller University Laboratory Animal Research Center, and were maintained in a controlled environment with a 12h/12h light/dark cycle. In the bile-duct cannulated experiments, one control and one metalloporphyrin-treated animal were studied together, as described in Biochem Biophys. Acta, 1981;673: 339-350 and J. Clin. Invest., 1985; 75: 513-521. Bile duct cannulation was performed in adult rats (330-400 grams) following barbiturate anesthesia (7.5 mg per 100 grams body weight, IP). The animals were prepared for surgery in the usual manner, the peritoneal cavity entered, and the common bile duct identified and isolated. A silk suture was tied around the duct just proximal to the pancreas. A small incision was made into the common bile duct just proximal to the first tie, and a length of polyethylene tubing was inserted into the duct. A doubly-tied ligature was then placed around the tubing and cut; the first ligature was also used as an additional stay suture for the tubing. A trochar was passed through the right lateral abdominal wall, and the end of the tubing passed to the outside through the trochar, which was then removed. An indwelling venous cannula was inserted at this time in the left jugular vein. This was attached to a Harvard infusion pump, set at a flow rate of 1.0 ml/h (5 percent dextrose in normal saline). The output of the bile duct cannula was attached to a fraction collector which collected a separate bile sample every 30 or 60 minutes in small pre-weighed collection tubes with self-contained caps. The externalized cannula, collecting device and tubes were kept under subdued light conditions throughout the collection periods.

Tissue preparation

Liver were perfused in situ with ice cold 0.9% NaCl and subsequently homogenized in 3 volumes of 0.1 M potassium phosphate buffer, pH 7.4, containing 0.25 M sucrose. Microsomal fractions were prepared as by Drummond and Kappas in Proc Natl. Acad. Sci., U.S.A., 1981; 78; 6466-6470, the description of which is fully incorporated herein by reference, for the determination of heme oxygenase in liver. Splenic microsomes were prepared in an identical manner. The cytosolic fraction obtained from the liver of control (saline-injected) animals served as a source of bilirubin reductase for subsequent analysis of heme oxygenase activity. Assays for heme oxygenase and metalloporphyrin concentration were performed on fresh microsomes whenever possible. Otherwise, microsomal fractions were kept at liquid nitrogen temperatures until the time of assay. No loss of enzyme activity or metalloporphyrin concentration was noted on storage.

Assays

The activity of heme oxygenase in tissues was determined as described by Drummond and Kappas, supra. Bilirubin formation was calculated using an absorption coefficient of $40 mM^{-1} cm^{-1}$ between 464 and 530 nm. Bilirubin concentrations in plasma and bile were determined by the fluorometric method of M. Roth in Clin. Chem. Acta, 1976; 17:487-492. Protein concentration was measured by the method of Lowry et al in J. Biol. Chem., 1951; 193:265-275, using crystalline BSA as a standard. Metalloporphyrin concentrations were determined by the fluorometric method of Simionatto et al, in Biological Samples, Anal. Biochem., 1984; 260:12198-12202. Standard settings for the two metalloporphyrins examined were:

| Material | Exciting Wavelength | Emitting Wavelength | Specific Fluorescence (Fluorescence Units/$\mu$M) |
|---|---|---|---|
| SnPP | 400 | 581 | 9,737 |
| SnMP | 392 | 571 | 16,680 |

Preparation of liposomes containing metalloporphyrin

Phosphatidyl choline, prepared from egg yolk (Sigma Chemical Co., St. Louis, Mo.), 100 mg/ml in chloroform) was addend to a round bottom flask. The metalloporphyrin, dissolved in chloroform: methanol (1:9), was then added and the contents evaporated to dryness in the dark in a rotary evaporator under vacuum (32° C., 15-45 minutes). Two ml aliquots of phosphate buffered saline (pH 7.4) at room temperature were then added to the flask, and the flask was vortexed vigorously until all material was removed from its sides. The contents were then collected and centrifuged at 15,000 xg for 5 minutes at 4° C. The supernatant solution was removed and the liposomal pellet was resuspended in buffer. The material was then centrifuged and re-washed until the supernatant was clear. When the ratio of phosphatidyl choline to metalloporphyrin (mg/mg) was greater than 10, incorporation of metalloporphyrin into liposomes was found to be in the range of 94-97 percent.

The metalloporphyrins thus incorporated into liposomes underwent brief sonication (25% power, 10 seconds) immediately prior to injection, in order to prevent the production of large aggregates. The sonication procedure did not cause significant leakage of metalloporphyrin into the supernatant. When prepared in this manner, liposomes could be injected intravenously into the animals without appreciable amounts becoming trapped as macroaggregates in the lungs. The results are shown in Table III below.

TABLE III

Organ Homogenate Localization Index $\frac{\mu M}{(\mu m/kg)}$

| Organ | Aqueous SnPP | Liposomal SnPP | Liposomal SnMP |
|---|---|---|---|
| Kidney | 2.5–3.6 | 0.0–0.2 | 0.3–0.5 |
| Liver | 0.4–0.9 | 0.6–0.9 | 1.7–2.4 |
| Spleen | 0.1–0.2 | 2.1–5.0 | 5.1–11.6 |
| Femoral marrow | 0.2 (1)* | 0.3–0.9 | 0.4–0.8 |
| Skin | 0.1 (1)* | 0.1 (1)* | — |
| Lung | 0.2–0.3 | 0.1–0.2 | — |

Results shown are total ranges for localization index for each organ and metalloporphyrin preparatin, with at least 4 observations, except where indicated.
*Number of observations in parentheses

RESULTS

Localization of metalloporphyrin in tissues

SnPP or SnMp was administered at doses of from 3–50/μmol/kg body weight. The aqueous preparations were injected either intravenously or subcutaneously while the liposomal preparations were injected by the IV route. Metalloporphyrin concentrations were then determined in the homogenates of liver, spleen, kidneys, lung, and femoral bone marrow. In order to facilitate comparisons between experiments, a "localization index" was derived, which normalized the concentration of metalloporphyrin in the tissue to the administered dose. For tissue homogenates this was expressed as:

$$\text{Localization index } \frac{(\mu M/\mu m/kg)} = \frac{\text{metalloporphyrin concentration } (\mu M)}{\text{metalloporphyrin dose } (\mu m/kg)}$$

As shown in Table III, when tissue distribution was compared 16–24 hours after injection, concentrations of metalloporphyrin in spleen were markedly (10–50-fold) higher after IV liposomal injection than after injection of the aqueous material. A smaller increase was noted in femoral marrow. The levels achieved in liver were substantially independent of the route of injection. Aqueous metalloporphyrin targeted primarily to the kidney and to a lesser extent liver, whereas the liposomal preparations did not target to the kidney to any significant extent. Metalloporphyrin concentration in the lungs was minimal by either route.

Inhibition of splenic and hepatic heme oxygenase

Adult males rats were injected IV with liposomal metalloporphyrins at a dose of 8–14μm/kg body weight and sacrificed at a number of time points to determine the activity of heme oxygenase in liver and spleen. It was found that splenic heme oxygenase was inhibited by greater than 90% within 30 minutes of injection, while hepatic heme oxygenase activity was inhibited up to 67% at the same time point. Levels of heme oxygenase activity in spleen and liver were determined 16–18h after metalloporphyrin injection, and also at the time of sacrifice of the bile duct cannulated animals. Longer-term experiments were performed to determine the extent of inhibition by assaying enzyme activity at 3–28 days post-injection. The results are shown in Table IV below.

TABLE IV

| Material/Preparation | Dose (μm/kg) | Elapsed Time | Metalloporphyrin concentration (pm/mg protein) | | Heme Oxygenase activity (nm bilirubin/hr/mg. protein) | |
|---|---|---|---|---|---|---|
| | | | Liver | Spleen | Liver | Spleen |
| Saline Controls | 0 | 16–24 h | ND* | ND | 2.3 ± 0.6** | 9.0 ± 2.4** |
| Aqueous SnPP | 10 | 16 hrs | 149 | 56 | 0.6 | 3.6 |
| | 50 | 16 hrs | 280 | 93 | 0.4 | 5.3 |
| | 10 | 48 hrs | 45 | 98 | 1.0 | 5.9 |
| | 50 | 48 hrs | 200 | 129 | 0.5 | 6.3 |
| Liposomal SnPP | 14 | 2 min | 75 | 35 | ND | 2.6 |
| | 12 | 30 min | 101 | 147 | 0.8 | ND |
| | 12 | 60 min | 152 | 132 | 0.6 | ND |
| | 12 | 90 min | 60 | 141 | 0.7 | 0.4 |
| | 14 | 18 hrs | 207 | 859 | 0.9 | 0.4 |
| Liposomal SnMP | 10 | 18 hrs | 229 | 3206 | 0.5 | ND |
| | 8 | 3 days | 26 | 1091 | ND | ND |
| | 8 | 7 days | 16 | 589 | 0.6 | 2.3 |
| | 8 | 11 days | 16 | 423 | 0.5 | 2.8 |
| | 8 | 17 days | 6 | 459 | ND | 3.6 |
| | 8 | 28 days | 2 | 57 | 1.0 | 2.1 |

*ND = Levels not detectible by available assay technique
**Mean ± SD
Each line in this table represents results in a single animal injected intravenously with the preparation listed. Results in the control animals represent, for heme oxygenase activity, mean ± SD for more than 30 duplicate assays.

The results in Table IV indicate that very high concentrations of metalloporphyrin and complete inhibition of splenic heme oxygenase were achieved for at least 3 days after IV liposomal injection of SnMP. Pronounced inhibition of splenic heme oxygenase persisted for as long as 28 days after injection of the liposome-encapsulated inhibitor.

Effect of metalloporphyrin preparations in bile duct-cannulated rats

Figure 3:
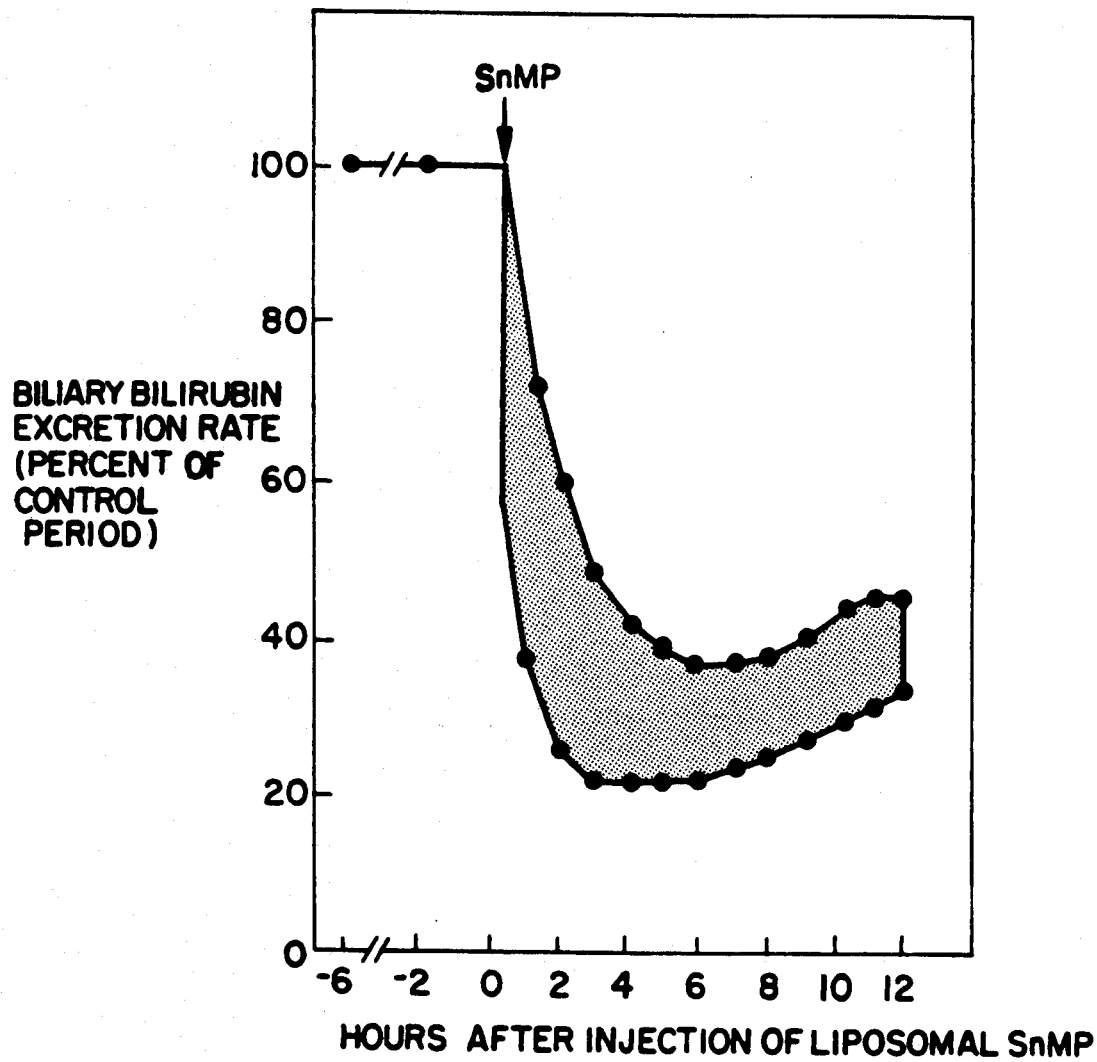
FIG. 3 is a graph illustrating the biliary bilirubin excretion rate as a function of time after injection of liposomal SnPP.

Liposomal SnMP, aqueous SnPP, saline, or empty liposomes were injected into bile duct-cannulated rats 4–6h after onset of collection of bile samples (5–7h after bile duct cannulation). When saline or empty liposomes were injected IV there was no reduction in the rate of bilirubin production (data not shown). When liposomal SnMP was given IV, a 50 percent reduction in bilirubin production was seen within 30–90 minutes, while maximal inhibition was seen at about 3–10h (FIG. 3). When compared with the biliary bilirubin excretion rate in the same animal prior to metalloporphyrin injection, liposomal SnMP inhibited bilirubin output by an average of 73 percent (range: 66-79 percent).

Referring now to FIG. 1, there is shown the effect of liposomes-bound SnPP and for comparison, RBC ghosts-bound SnPP, on inhibition of splenic heme oxygenase in rats after 16-18 hours after the injection. As is shown in this figure, following injection of aqueous SnPP, splenic microsomal SnPP concentrations do not exceed about 100 pm/mg protein, whereas concentrations over 600 pm/mg protein are achieved with liposomal SnPP.

Figure 2:
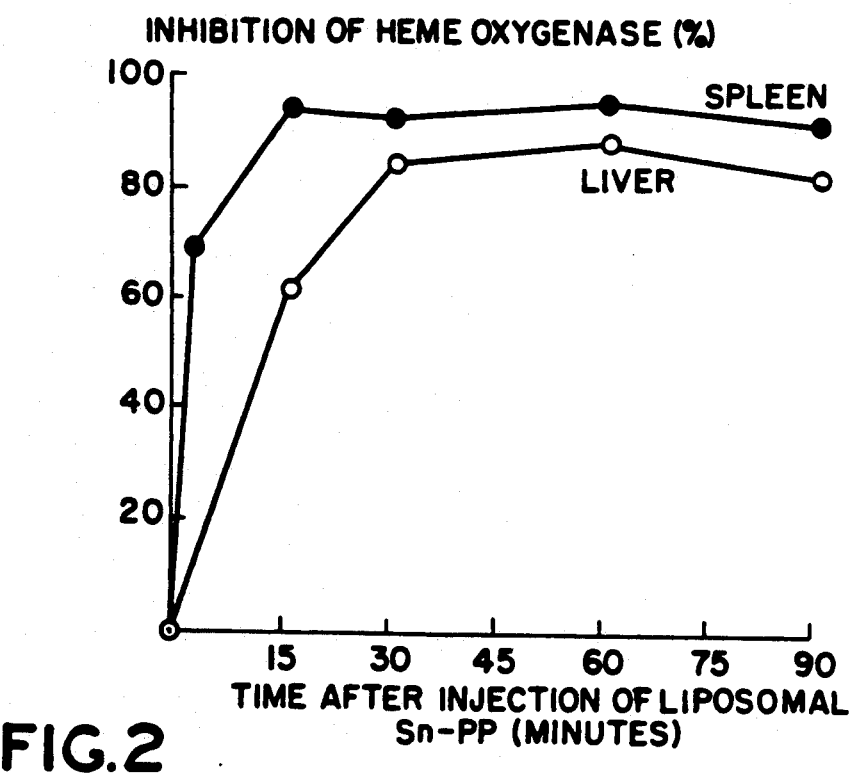
FIG. 2 is a graph illustrating the time course of inhibition of splenic and hepatic heme oxygenase after intravenous injection of liposomal SnPP in adult rats.

FIG. 2 shows the percent heme oxygenase inhibition in the spleen and liver as a function of time after intravenous injection of liposomal SnPP in adult rats. The data in this figure were obtained by injecting adult rats intravenously with 10 $\mu$/kg of liposomal SnPP. The rats were sacrificed at varying times after injection for measurements of hepatic and splenic heme oxygenase activity. As it is noted from this figure, splenic heme oxygenase activity was inhibited by more than 90% within approximately 15 minutes of the injection. Also, about 60% inhibition of hepatic heme oxygenase activity was noted during approximately the same period.

In FIG. 3, the biliary bilirubin excretion in the bile-duct cannulated rats injected intravenously by liposomal SnPP is plotted as the ordinate, versus the time, in hours, after the injection of the liposomal SnPP, as the abscissa. The closed circles represent the data obtained in a single animal, while the shaded area represents the total range noted in four rats injected with 8 $\mu$m/kg body weight of SnPP. The arrow in this figure indicates the time of injection of SnPP. In all cases, inhibition was measured as a percentage of pre-injected bilirubin excretion rate, averaged over 4 to 6 hours immediately prior to injection.

As shown in FIG. 3, when liposomal SnPP was injected intravenously, a 50% reduction in bilirubin production rate was observed within 30-90 minutes, while maximum inhibition was observed at about 3-10 hours after injection of the SnPP.

Similar results as those described hereinabove are found with other tin porphyrins identified herein.

Thus, as can be appreciated from the foregoing detailed description, the drawings and the data shown in the tables, the present invention provides a composition which when parenterally administered into mammals, selectively targets the spleen and thereby inhibits or substantially reduces the splenic heme oxygenase activity. This is highly significant and advantageous clinically since such inhibition results in considerable and clinically significant reduction in the rate of heme metabolism and the production of undesirable bilirubin and carbon monoxide in mammals.

Although the present invention was described in detail using SnPP as the metalloporphyrin, other metalloporphyrin may be used efficaciously as heme oxygenase inhibitors. For example, it has been found that while ZnPP is relatively ineffective when used at the same concentrations as SnPP, if however ZnPP is administered with liposomes, the activity of ZnPP will be raised to a level which is substantially comparable to the efficacy of SnPP.

Similar results are obtained with other zinc porphyrins used in the practice of this invention.

Liposomal chromium porphyrins of the class defined herein may be similarly employed. This is surprising since CrPP exhibits some toxicity if used in isotonic aqueous media at the same level as SnPP. If used as liposomal CrPP, however, the effective dosage levels are sufficiently low so that no toxicity is observed.

Surprisingly, MnPP which is ineffective in lowering plasma bilirubin levels in newborn animals, becomes effective when used in conjunction with a liposome.

The data in the following tables illustrate the efficacy of liposomal manganese mesoporphyrins, chromium mesoporphyrins and zinc mesoporphyrins as heme oxygenase inhibitors and the ability of these metalloporphyrins to target the spleen.

TABLE V

| Treatment | Heme oxygenase activity (n mol bilirubin/mg/hr.) | |
|---|---|---|
| | Liver | Spleen |
| Saline | 10.5 ± 4.5(100) | 20.8 ± 7.2(100) |
| Liposomal MnMP | 7.6 ± 4.5(72.4)* | 12.1 ± 4.3(58.2)* |
| Liposomal CrMP | 1.5 ± 0.2(21.7)* | 3.8 ± 1.8(18.3)* |

*Percent reduction from control value with saline.

The data in Table V were obtained in bile duct cannulated rats by administering the liposomal metalloporphyrin intravenously at a dosage of 8 $\mu$mol/kg body weight.

The data in Tables V and VI below illustrate the ability of liposomal manganese mesoporphyrins and chromium mesoporphyrins, respectively, to target the spleen.

TABLE VI

| Treatment | Manganese ($\mu$g/mg microsomal protein) | |
|---|---|---|
| | Liver | Spleen |
| Aqueous MnMP | 0.0075 ± 0.001 | 0.004 ± 0.002 |
| Liposomal MnMP | 0.0063 ± 0.001 | 0.014 ± 0.005 |

As with the data obtained for Table V, the liposomal MnMP was administered to bile duct cannulated rats intravenously at a dose of 8 $\mu$mol/kg body weight.

TABLE VII

| Treatment | Chromium ($\mu$g/mg microsomal protein) | |
|---|---|---|
| | Liver | Spleen |
| Aqueous CrMP | 0.026 ± 0.002 | 0.064 ± 0.010 |
| Liposomal CrMP | 0.037 ± 0.004 | 0.139 ± 0.03* |

*p < 0.5 when compared with aqueous CrMP.

The data obtained for Table VII were also obtained on bile duct cannulated rats by administering the liposomal metalloporphyrin intravenously at a dosage of 8 $\mu$mol/kg body weight.

The use of liposomal metalloporphyrins in accordance with this invention also results in clinically significant decrease in biliary bilirubin. The results are shown in Table VIII. These data were obtained on bile duct cannulated rats by intravenous administration of the liposomal compound at a dosage of 8 $\mu$mol/kg body weight.

TABLE VIII

| Treatment | Percent decrease in biliary bilirubin* |
|---|---|
| Liposomal ghosts | 7.5 |
| Liposomal MnMP | 33.0 |
| Liposomal ZnMP | 38.0 |
| Liposomal CrMP | 54.0 |
| Liposomal SnMP | 58.0 |

*The percent decrease is the difference between control periods (4-6 hours) prior to administration of the liposomal compounds and treatment period (4-6 hours) where the maximum decrease in bilirubin occurred.

Thus, as shown in Tables V to VIII the administration of the liposomal manganese metalloporphyrins, liposomal chromium metalloporphyrins and liposomal zinc metalloporphyrins of the invention in mammals result in clinically effective concentrations of these compounds in the spleen with concommitant decrease in heme oxygenase activity and biliary bilirubin production. Also, while the data in Tables V to VIII have been illustrated by using mesoporphyrins incorporated within liposomes, similar advantageous results are obtained by using the corresponding liposomal protoporphyrins and liposomal diiododeuteroporphyrins.

In the foregoing description of the invention, the use of a particular class of liposomes, i.e., phospholipid vesicles, was described in conjunction with selected metalloporphyrins for purposes of illustration. However, the invention is not limited to this particular class of liposomes since the advantages of the present invention are achieved with other types of liposomes.

The liposomal metalloporphyrins of this invention may be administered to mammals parenterally; however, intravenous administration is preferred. These compositions are normally administered in therapeutically effective doses which vary depending on the particular metalloporphyrin which is employed. Broadly, the tin porphyrins are used in dosages ranging from about 0.1 to about 50 m/kg body weight. When using SnPP or SnDDP, the dosage level can vary from about 0.5 to about 50 m/kg body weight, whereas when using SnMP, the dosage level may be lower, ranging from about 0.1 to about 15 μm/kg body weight.

If the metalloporphyrin employed is a Cr, Zn or Mn porphyrin, the dosage level may vary widely from about 0.1 to about 50 m/kg body weight.

The liposomal metalloporphyrins of this invention may be used alone or in a pharmaceutically acceptable carriers known to those skilled in the art, such as in buffered aqueous solutions made isotonic by the addition of sodium chloride, glucose or other standard solutes.

In order to administer dosages ranging from about 0.1 to about 50 μm/kg body weight in the case of tin porphyrins, dosage units are provided which contain from about 0.07 to about 46 mg/dosage unit. If the metalloporphyrin employed is SnPP or SnDPP, the dosage unit can vary from about 0.35 to about 46 mg/dosage unit, while lower amounts of from about 0.07 to about 11 unit is sufficient for SnMP.

If the metalloporphyrin employed is a Cr, Zn or Mn porphyrin, the concentration may vary from about 1 to about 50 mg per dosage unit.

In general, it has been found that Cr porphyrins are more effective than Zn porphyrins while Zn porphyrins are more effective than Mn porphyrins.

Also, as is apparent from the results described above, the mesoporphyrins are more effective than the other porphyrins and hence they are preferred for use in the present invention.

What is claimed is:

1. A pharmaceutical composition for improved inhibition of heme oxygenase activity in mammals comprising a liposomal metalloporphyrin, the metalloporphyrin component of which is a heme oxygenase inhibitor.

2. A composition as in claim 1 wherein said metalloporphyrin is selected from the group consisting of tin, chromium, zinc and manganese protoporphyrin, mesoporphyrin and diiododeuteroporphyrin, and mixtures thereof.

3. A composition as in claim 1 further comprising a pharmaceutically acceptable carrier.

4. A composition as in claim 1 wherein said metalloporphyrin is tin protoporphyrin, tin mesoporphyrin or tin diiododeuteroporphyrin.

5. A composition as in claim 4 further including a pharmaceutically acceptable carrier.

6. A composition as in claim 1 in dosage unit form containing from about 0.07 to about 46 mg/dosage unit.

7. A composition as in claim 2 in dosage unit form containing from about 0.07 to about 46 mg/dosage unit.

8. A composition as in claim 3 in dosage unit form containing from about 0.07 to about 46 mg/dosage unit.

9. A composition as in claim 4 in dosage unit form containing from about 0.07 to about 46 mg/dosage unit.

10. A method of improving the inhibition of heme oxygenase activity in mammals in need of such inhibition which comprises intravenous administration of liposomal metalloporphyrin in an amount sufficient to effect such inhibition, wherein the metalloporphyrin is a heme oxygenase inhibitor.

11. A method as in claim 10 wherein said metalloporphyrin is selected from the group consisting of tin, chromium, zinc and manganese protoporphyrin, mesoporphyrin and diiododeuteroporphyrin and mixtures thereof.

12. A method as in claim 10 wherein said metalloporphyrin is in a pharmaceutically acceptable carrier.

13. A method as in claim 10 wherein metalloporphyrin is tin protporphyrin, tin mesoporphyrin and tin diiododeuteroporphyrin.

14. A method as in claim 13 wherein said metalloporphyrin is in a pharmaceutically acceptable carrier.

15. A method as in claim 10 wherein said metalloporphyrin is a dosage unit form containing from about 0.07 to about 46 mg/dosage unit.

16. A method as in claim 11 wherein said metalloporphyrin is in dosage unit form containing from about 0.07 to about 46 mg/dosage unit.

17. A method as in claim 12 wherein said metalloporphyrin is in dosage unit form containing from about 0.07 to about 46 mg/dosage unit.

18. A method as in claim 13 wherein said metalloporphyrin is in dosage unit form containing from about 0.07 to about 46 mg/dosage unit.

19. A method as in claim 14 wherein said metalloporphyrin is in dosage unit form containing from about 0.07 to about 46 mg/dosage unit.

20. A method as in claim 10, 11, 12, 13, 14, 15, 16, 17, 18 or 19 wherein said mammal is human.

* * * * *